US011559357B2

(12) United States Patent
Barbagli et al.

(10) Patent No.: US 11,559,357 B2
(45) Date of Patent: Jan. 24, 2023

(54) SYSTEMS AND METHODS FOR NAVIGATING TO A TARGET LOCATION DURING A MEDICAL PROCEDURE

(71) Applicant: INTUITIVE SURGICAL OPERATIONS, INC., Sunnyvale, CA (US)

(72) Inventors: Federico Barbagli, San Francisco, CA (US); Simon P. DiMaio, San Carlos, CA (US); Gary S. Guthart, Los Altos, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 432 days.

(21) Appl. No.: 16/623,260

(22) PCT Filed: Jun. 21, 2018

(86) PCT No.: PCT/US2018/038827
§ 371 (c)(1),
(2) Date: Dec. 16, 2019

(87) PCT Pub. No.: WO2018/237187
PCT Pub. Date: Dec. 27, 2018

(65) Prior Publication Data
US 2020/0179058 A1 Jun. 11, 2020

Related U.S. Application Data

(60) Provisional application No. 62/524,202, filed on Jun. 23, 2017.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *G01N 33/48* (2013.01);
(Continued)

(58) Field of Classification Search
CPC ......... A61B 34/30; A61B 34/10; A61B 34/20; A61B 34/35; A61B 34/76; A61B 5/066;
(Continued)

(56) References Cited

U.S. PATENT DOCUMENTS 5,411,888 A * 5/1995 Gordon .............. A61K 49/0006
436/63
6,380,732 B1 4/2002 Gilboa
(Continued)

FOREIGN PATENT DOCUMENTS

CN 101108140 A 1/2008
CN 102149334 A 8/2011
(Continued)

OTHER PUBLICATIONS

Dent, A.G., et al., "Exhaled Breath Analysis for Lung Cancer," Journal of Thoracic Disease, Oct. 2013, vol. 5 (5), pp. S540-S550.
(Continued)

*Primary Examiner* — Brenda C Bernardi
(74) *Attorney, Agent, or Firm* — Haynes and Boone, LLP

(57) ABSTRACT

The systems and methods of the present disclosure are used for guiding a medical instrument towards a target, the method positioning a medical instrument at a first location within a patient anatomy, wherein the medical instrument comprises at least one sensor, determining a first biomarker measurement using the at least one sensor, determining a second biomarker measurement using the at least one sensor, comparing the first biomarker measurement with the second biomarker measurement to determine a proximity to the target to provide a first comparison, and providing guidance
(Continued)

for moving the medical instrument based on results of the first comparison.

20 Claims, 9 Drawing Sheets

(51) Int. Cl.
*G01N 33/48* (2006.01)
*A61B 34/30* (2016.01)

(52) U.S. Cl.
CPC . *A61B 2034/101* (2016.02); *A61B 2034/2051* (2016.02); *A61B 2034/301* (2016.02); *A61B 2562/02* (2013.01)

(58) Field of Classification Search
CPC .......... A61B 2017/00809; A61B 18/22; A61B 2034/2051; A61B 2562/02; A61B 2034/2061; A61B 2034/101; A61B 2017/00035; A61B 2090/378; A61B 2034/301; A61B 2090/376; A61B 2090/374; A61B 2090/3762; A61B 2090/3735; G01N 33/48
See application file for complete search history.

(56) References Cited

U.S. PATENT DOCUMENTS

| | | | |
|---|---|---|---|
| 6,389,187 | B1 | 5/2002 | Greenaway et al. |
| 7,772,541 | B2 | 8/2010 | Froggatt et al. |
| 8,900,131 | B2 | 12/2014 | Chopra et al. |
| 9,452,276 | B2 | 9/2016 | Duindam et al. |
| 2002/0128570 | A1 | 9/2002 | Bowman et al. |
| 2003/0073900 | A1 | 4/2003 | Senarith et al. |
| 2006/0013523 | A1 | 1/2006 | Childlers et al. |
| 2007/0180933 | A1* | 8/2007 | Grate .................. G01N 1/2214 73/863.12 |
| 2008/0214931 | A1 | 9/2008 | Dickfeld et al. |
| 2010/0081964 | A1 | 4/2010 | Mark et al. |
| 2011/0201956 | A1* | 8/2011 | Alferness .............. A61B 5/0878 600/529 |
| 2011/0263950 | A1* | 10/2011 | Larson ................ A61B 5/6892 600/595 |
| 2013/0096385 | A1 | 4/2013 | Fenech et al. |
| 2013/0253288 | A1 | 9/2013 | Agmon et al. |
| 2014/0051986 | A1 | 2/2014 | Zhao et al. |
| 2014/0067036 | A1 | 3/2014 | Shuros et al. |
| 2014/0275991 | A1 | 9/2014 | Potter et al. |
| 2016/0341712 | A1 | 11/2016 | Agar |

FOREIGN PATENT DOCUMENTS

| | | |
|---|---|---|
| CN | 102316817 A | 1/2012 |
| CN | 102326078 A | 1/2012 |
| CN | 104271062 A | 1/2015 |
| WO | WO-2010079490 A1 | 7/2010 |
| WO | WO-2014058838 A1 | 4/2014 |
| WO | WO-2016032846 A1 | 3/2016 |
| WO | WO-2016191298 A1 | 12/2016 |

OTHER PUBLICATIONS

International Preliminary Report on Patentability for Application No. PCT/US2018/038827, dated Jan. 2, 2020, 11 pages.
International Search Report and Written Opinion for Application No. PCT/US2018/038827, dated Dec. 5, 2018, 15 pages.
Mazzone, P.J. et al., "Diagnosis of Lung Cancer by the Analysis of Exhaled Breath with a Colorimetric Sensor Array," Thorax, Jul. 2007, vol. 62 (7), pp. 565-568.
Schmidt, K., et al., "Current Challenges in Volatile Organic Compounds Analysis as Potential Biomarkers of Cancer," Journal of Biomarkers, Mar. 2015, vol. 2015, pp. 1-16.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18820081.0 dated Feb. 19, 2021, 09 pages.
Office Action for Chinese Application No. CN20188008924, dated Oct. 10, 2022, 42 pages.

* cited by examiner

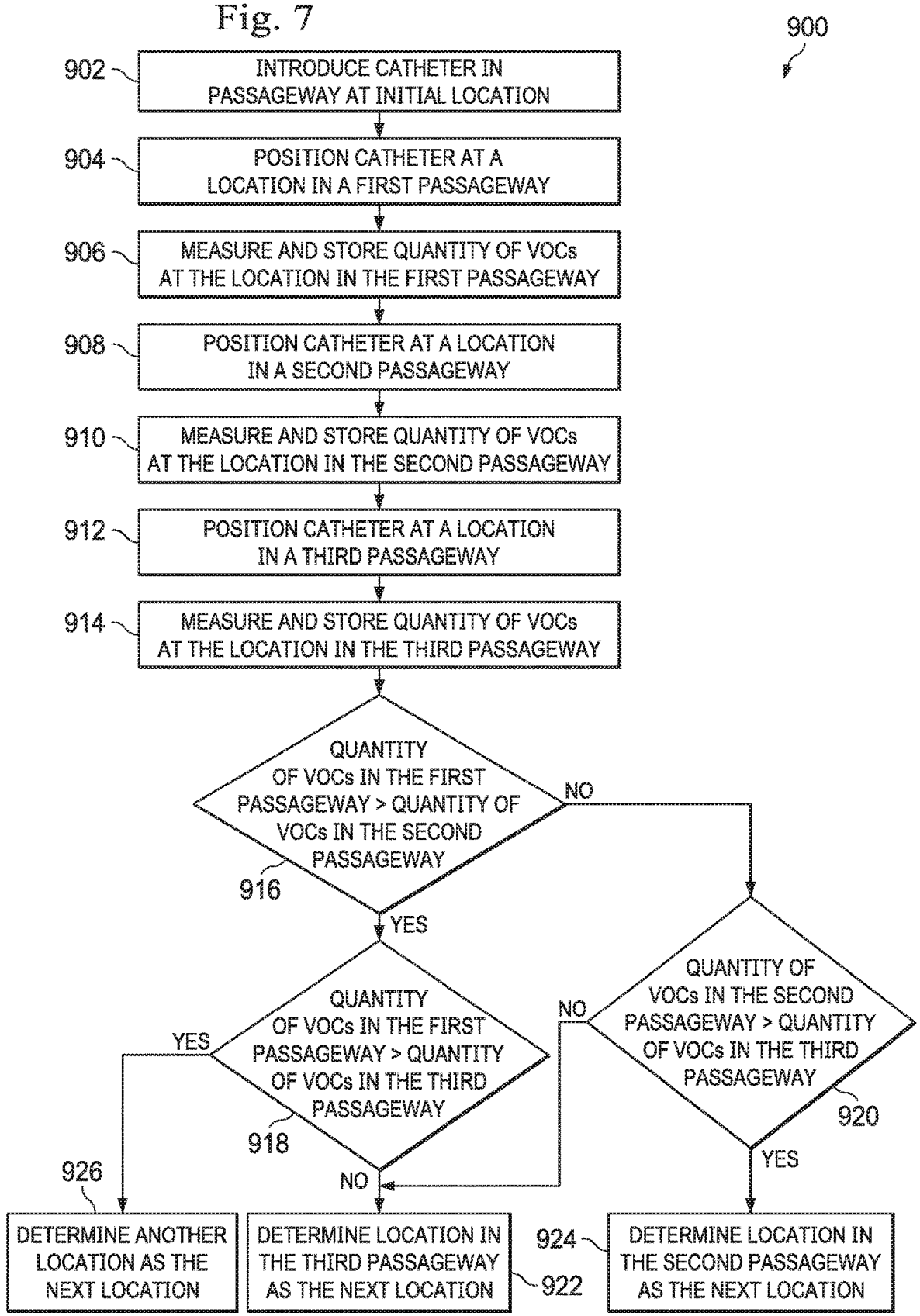

SYSTEMS AND METHODS FOR NAVIGATING TO A TARGET LOCATION DURING A MEDICAL PROCEDURE

CROSS-REFERENCE TO RELATED APPLICATIONS

This patent application is the U.S. national phase of International Application No. PCT/US2018/038827, filed Jun. 21, 2018, which designated the U.S. and claims priority to and the benefit of the filing date of U.S. Provisional Patent Application 62/524,202 filed Jun. 23, 2017 which is incorporated by reference herein in their entireties.

FIELD

The present disclosure is directed to systems and methods for conducting a surgical procedure to precisely detect a location of a mass (e.g., tumor) in a patient's body by sensing and analyzing biomarkers, such as volatile organic compounds (VOCs), present in the vicinity of the mass. The surgical procedure may be a visually guided procedure and may allow the display of pathology data sampled during the surgical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomical systems such as the lungs, the colon, the intestines, the kidneys, the heart, the circulatory system, or the like. Traditional instrument tracking systems, including electromagnetic sensing tracking systems, may disturb the clinical environment or workflow. Therefore, systems and methods for performing image guided surgery with minimal clinical disturbances are needed. Further, when the pre-operative or intra-operative images of the patient anatomy are unavailable, systems and methods for performing surgical procedures involving navigation of medical instruments to reach a target tissue location are needed.

SUMMARY

The embodiments of the invention are summarized by the claims that follow the description.

In one embodiment, a method performed by a computing system may include using a catheter to traverse a first anatomical passageway to place a distal end of the catheter at a first position within the first anatomical passageway and a second anatomical passageway to place the distal end of the catheter at a second position within the second anatomical passageway. The method may also include using a sensor to detect presence of volatile organic compounds (VOCs) at the first position and at the second position. Then, the method may include determining a first quantity of the VOCs detected at the first position and a second quantity of the VOCs detected at the second position, and comparing the first quantity of the VOCs with the second quantity of the VOCs. The method may then effect movement of the catheter within the first anatomical passageway or within the second anatomical passageway based on the results of the comparison.

In another embodiment, a method may include using a catheter to traverse a first anatomical passageway to place a distal end of the catheter at a first position and a second position within the first anatomical passageway. The method may then include detecting, via a sensor, presence of volatile organic compounds (VOCs) at the first position and at the second position, determining a first quantity of the VOCs at the first position and a second quantity of the VOC that the second position, and comparing the first quantity of the VOCs with the second quantity of the VOCs. The method may also include effecting movement of the catheter within the first anatomical passageway based on the results of the comparison.

In another embodiment, a system comprises a teleoperational assembly including an operator control system and a manipulator configured for teleoperation by the operator control system. The manipulator is configured to control movement of a medical instrument in a surgical environment. The system also comprises a processing unit including one or more processors. The processing unit is configured to traverse, using a catheter, a first anatomical passageway to place a distal end of the catheter at a first position within the first anatomical passageway and a second anatomical passageway to place the distal end of the catheter at a second position within the second anatomical passageway. The processor may then be configured to detect, via a sensor, presence of volatile organic compounds (VOCs) at the first position and at the second position, to determine a first quantity of the VOCs at the first position and a second quantity of the VOCs at the second position, and to compare the first quantity of the VOCs with the second quantity of the VOCs. The processor may be further configured to effect movement of the catheter within the first anatomical passageway or within the second anatomical passageway based on the results of the comparison.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7 is a flowchart illustrating a general method 900 used to provide guidance during a surgical procedure according to an embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
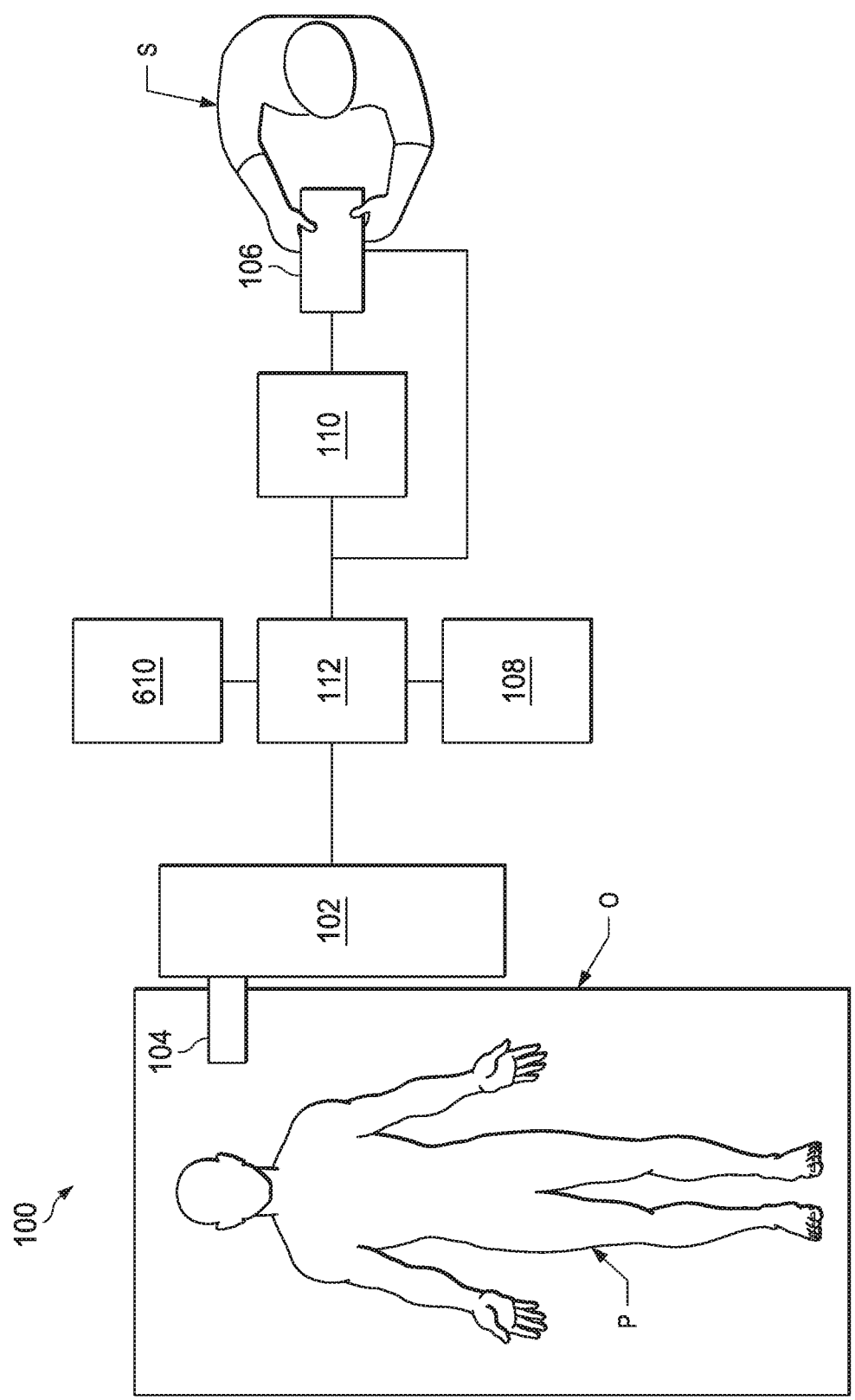
FIG. 1 is a teleoperated medical system accordance to an embodiment of the present disclosure.

Referring to FIG. 1 of the drawings, a teleoperated medical system for use in, for example, surgical, diagnostic, therapeutic, or biopsy procedures, is generally indicated by the reference numeral 100. As shown in FIG. 1, the teleoperated system 100 generally includes a teleoperational manipulator assembly 102 for operating a medical instrument 104 in performing various procedures on the patient P. The assembly 102 is mounted to or near an operating table O. A master assembly 106 allows the clinician, operator, surgeon S, and/or the like, to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like.

The manipulator assembly 102 supports the medical instrument system 104 and may include a kinematic structure of one or more non-servo controlled links (e.g., one or more links that may be manually positioned and locked in place, generally referred to as a set-up structure) and a manipulator manipulator. The manipulator assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the manipulator assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the manipulator assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 4A) may include a viewing scope assembly that records a concurrent or real-time image of the surgical site and provides the image to the clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions corresponding to processes disclosed herein.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the manipulator assembly 102, another portion of the processing being performed at the operator input system 106, and the like.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing manipulator assembly 102 to move the medical instrument system(s) 104 which extend into an internal surgical site within the patient body via openings in the body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomical passageways. Software alone or in combination with manual input is used to convert the recorded images into segmented two dimensional or three dimensional composite representation of a partial or an entire anatomical organ or anatomical region. An image data set is associated with the composite representation.

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 4A:
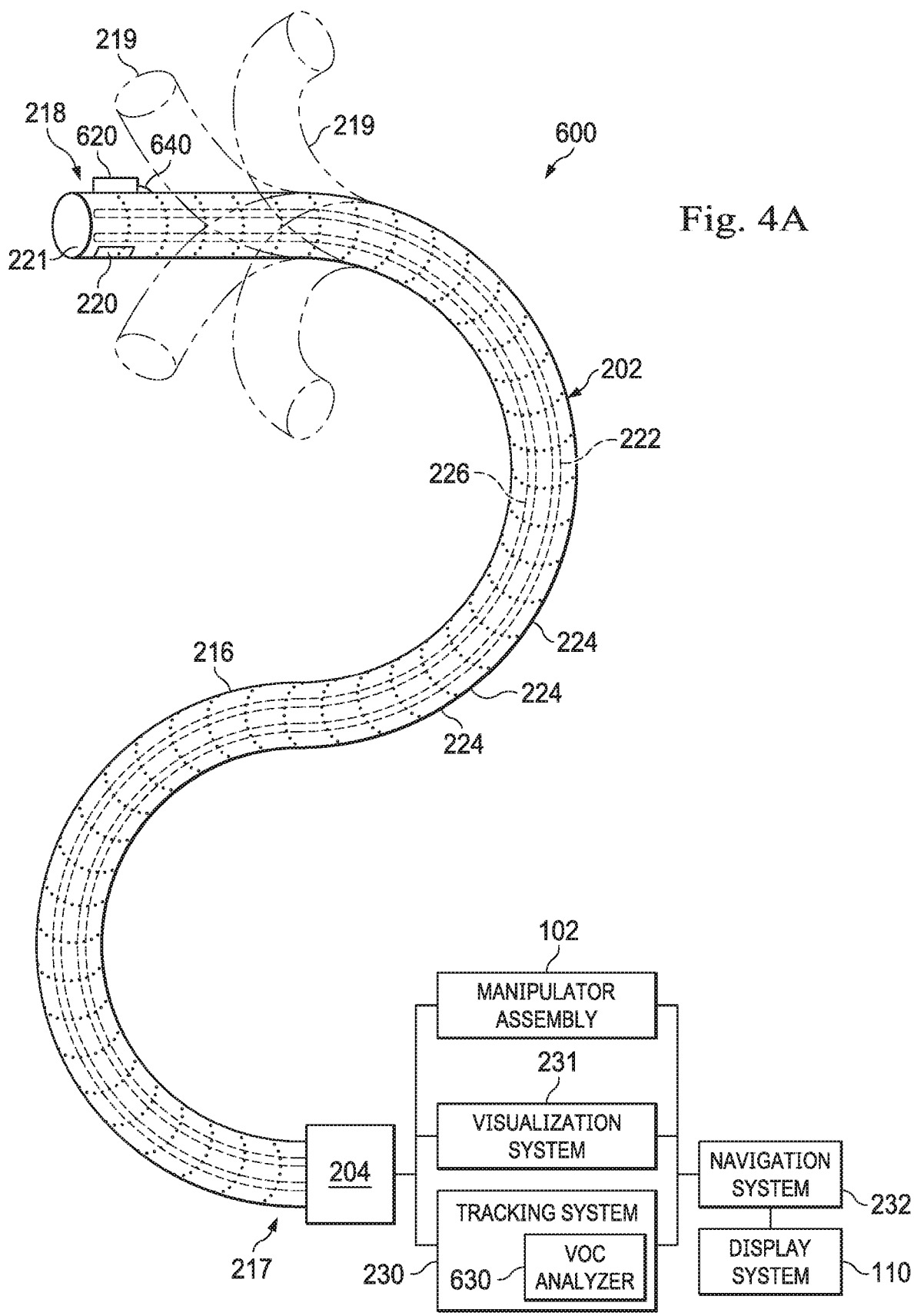
FIG. 4A illustrates a medical instrument system 600 that includes a visual device according to an embodiment of the present disclosure.

FIG. 4A illustrates a medical instrument system 600. Alternatively, the medical instrument system 600 may be used for non-teleoperational exploratory procedures or in procedures involving traditional manually operated medical instruments, such as endoscopy. Additionally or alternatively the medical instrument system 600 may be used to gather (i.e., measure) a set of data points corresponding to locations with patient anatomic passageways.

The instrument system 600 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216.

The shape sensor 222 may include an optical fiber aligned with the flexible catheter body 216 (e.g., provided within an interior channel (not shown) or mounted externally). The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, a series of positional sensors, such as EM sensors, positioned along the catheter can be used for shape sensing. Alternatively, a history of data from a positional sensor, such as an electromagnetic (EM) sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument 202.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 600 is actuated by a teleoperational assembly, the housing 204 may include drive inputs that removably couple to and receive power from motorized drive elements of the teleoperational assembly. In embodiments in which the instrument system 600 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 600. The control system 112 may utilize the position information as feedback for positioning the instrument 600. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 4A, the instrument 600 is teleoperated within the teleoperational medical system 100. In an alternative embodiment, the manipulator assembly 102 may be replaced by direct operator control. In the direct operation alternative, various handles and operator interfaces may be included for hand-held operation of the instrument.

Medical tool(s) 628 for such procedures as surgery, biopsy, ablation, illumination, irrigation, or suction can be deployed through the channel 221 of the flexible body 216 and used at a target location within the anatomy. If, for example, the tool is a biopsy instrument, it may be used to remove sample tissue or a sampling of cells from a target anatomical location. The medical tool may be used with an image capture probe also within the flexible body 216. Alternatively, the tool may itself be the image capture probe. The tool may be advanced from the opening of the channel 221 to perform the procedure and then retracted back into the channel when the procedure is complete. The medical tool may be removed from the proximal end 217 of the catheter flexible body or from another optional instrument port (not shown) along the flexible body.

Figure 2:
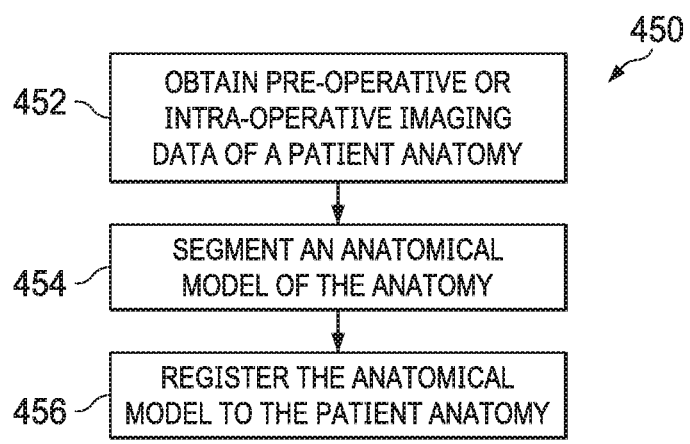
FIG. 2 is a flowchart illustrating a method used to provide guidance in an image guided surgical procedure according to an embodiment of the present disclosure.

FIG. 2 is a flowchart illustrating a general method 450 for use in an image guided surgical procedure. At a process 452, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs.

At a process 454, computer software alone or in combination with manual input is used to convert the recorded images into a segmented two dimensional or three dimensional composite representation or model of a partial or an entire anatomical organ or anatomical region.

At a process 456, the anatomic model data is registered to the patient anatomy prior to and/or during the course of an image-guided surgical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique described elsewhere in this disclosure. Other point set registration methods may also be used in registration processes within the scope of this disclosure.

Various systems for using sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery"), which is incorporated by reference herein in its entirety, discloses such systems.

Existing systems and methods often do not enable diagnosis of diseases such as cancer during their early stages. This is because the existing systems and methods rely upon detection of clinical symptoms, which are often silent during the early stages and do not manifest until the disease has progressed to an advanced stage. The lack of manifestation of characteristic clinical symptoms during the early stages of cancer renders early detection of the disease very difficult. Also, existing systems and methods performed to diagnose cancer either require invasive surgical procedures or are accompanied by undesirable exposure to radiation and high false-positive rates. As such, the present systems and methods are not effective for early diagnosis of life-threatening diseases such as cancer. Therefore, there is a need for new systems and methods that enable early diagnosis of life-threatening diseases.

The present disclosure proposes systems and methods that enable early diagnosis and, therefore, crucial timely treatment, for individuals suffering from life-threatening diseases. In particular, as discussed below in further detail, the systems and methods of the present disclosure enable precise detection of the location of a mass (e.g., tumor) in a patient's body by sensing and analyzing characteristics of biomarkers, such as VOCs, present in the vicinity of the mass. Sensed characteristics can include detection of biomarkers, various changes in the detected biomarkers including gradient changes, and a volatile metabolomic signature of biomarkers. In some implementations, the disclosed system and method can include identifying and detecting the volatile metabolomics signature of VOCs emitted by the target mass and navigating along anatomical passageways based on a change in strength of the volatile metabolomics signature detected. Detecting the volatile metabolomics signature can include filtering out presence of any background VOCs that are not attributed to the volatile metabolomics signature of the target mass. Although several examples are presented using VOCs as the detected and analyzed biomarker, the detection and analysis of biomarkers and changes in biomarkers, including gradient differences for other types of biomarker is provided further below. In addition to VOCs, suitable biomarkers may include pressure, oxygen levels, pH levels, and/or fluoroscopic properties.

The present disclosure includes realizations that detection and analysis of biomarkers, such as VOCs, may serve as a safe and noninvasive or minimally invasive way that enables early detection of cancer. VOCs are a diverse group of carbon-based chemical particles that are produced by masses (e.g., cancerous tumors) existing in a patient's body. These VOCs are unique characteristic compounds which identify the presence of the masses, and are produced in varying concentrations during physiological processes that are different from normal bodily physiological processes. Therefore, these VOCs may serve as potential biomarkers for assessment or diagnosis of the disease (e.g., cancer). Moreover, upon formation of the mass/tumor, the VOCs may be produced and discharged via the blood stream, interstitial fluid, lymphatic fluid, or other bodily fluids (including gases) into the anatomical passageways such as, for example, the endobronchial cavity of the patient. That is, the VOCs may be produced and may exist in the anatomical passageways of the patient prior to manifestation of any clinical symptoms of the disease. The systems and methods of the present disclosure use noninvasive procedures to detect and analyze these VOCs in the anatomical passageways, thereby enabling safe and effective early diagnosis of the disease.

Figure 3:
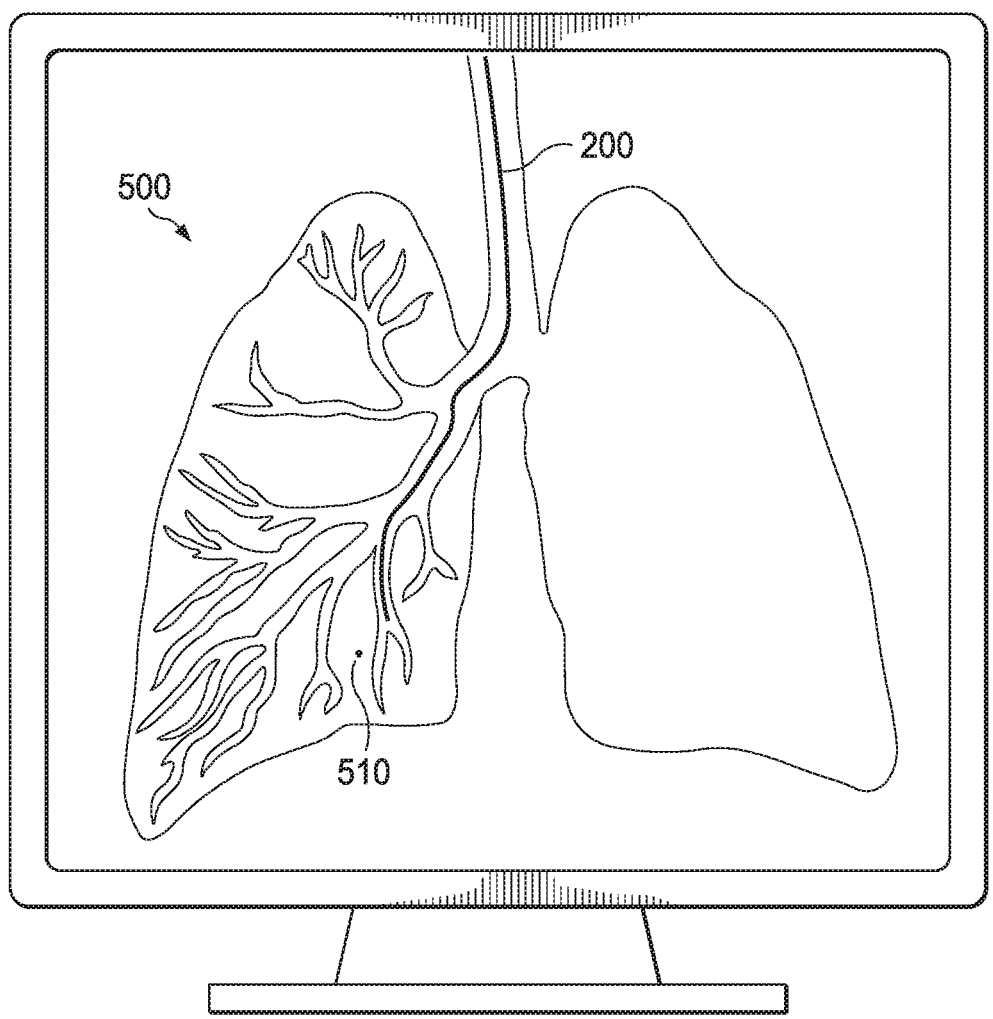
FIG. 3 illustrates a model of human lungs based on pre-operative or intra-operative image data.

FIG. 3 illustrates a model 500 of the patient's lungs 201 developed from pre-operative or intra-operative image data. In model 500, a mass/tumor 510 is observed as well as a virtual rendering of the catheter system 600 within the model 500. A medical procedure to biopsy the mass/tumor 510 may be conducted to determine whether the mass/tumor 510 is malignant or benign. Even though the location of the mass/tumor 510 is visible in the model, it may not be easy to determine the optimum position of the catheter system 600 relative to the mass/tumor 510 within the passageways of the patient's lungs 201 to conduct the biopsy. This may be due to shifting of anatomy between when pre-operative data is collected and performance of the surgical procedure for the biopsy as well as shifts in anatomy due to respiration, circulation, or patient movement. For these reasons, it is crucial to compensate for any discrepancies between the passageways within the patient's lungs displayed in model 500 and the actual passageways within the patient's lungs during the surgical procedure.

As discussed below, systems and methods of the present disclosure compensate for the above discrepancies by sensing and analyzing VOCs present in the vicinity of the mass/tumor 510. For example, the catheter system 600 of the present disclosure may be coupled with a sensor system capable of sensing and analyzing characteristic VOCs produced by the mass/tumor 510. In various embodiments, the sensor system may sense and report a quantity of VOCs in the passageways of the patient's lungs 201 in the vicinity of the mass/tumor 510. The reports from the sensor system may be received periodically or upon activation by the operator (e.g., clinician, surgeon, etc.). Based on the assumption that the density of the VOCs in the anatomical passageways is greater closer to the mass/tumor 510, a clinician/operator/surgeon performing the surgical procedure may review the information in the received reports, and may navigate different anatomical passageways of the patient's lungs accordingly. The clinician may then determine an optimum catheter distal tip location and/or position (e.g. direction and angle of approach of catheter distal tip) in a selected anatomical passageway of the patient's lungs 201 for placement of the catheter 202 closest to the mass/tumor 510 for the biopsy. In other words, based on a gradient of the quantity of VOCs, the sensor system may assist navigation of the different passageways. This may advantageously allow for selection of the optimum location and/or position, where the density of the VOCs is sensed to be the highest, for placement of the distal end 218 for the biopsy.

Figure 4B:
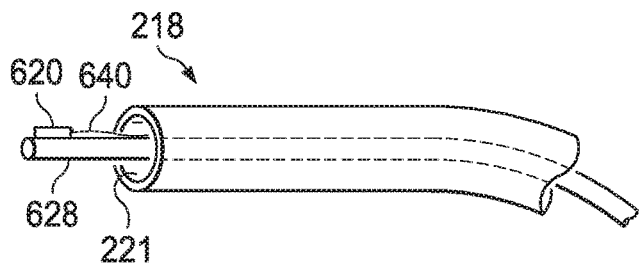
FIG. 4B illustrates a distal end of the medical instrument system of FIG. 4A with an extended medical tool that includes a visual device.

FIGS. 4A and 4B illustrate a medical instrument system 600 utilizing aspects of the present disclosure. In various embodiments, the medical instrument system 600 may include the entire catheter system 600 described above with respect to FIGS. 4A and 4B. In addition, the medical instrument system may be coupled with a sensor system 610. The sensor system 610 is illustrated in FIG. 1, and may include a set of distributed components. For example, the sensor system 610 may include a biomarker sensor (e.g., a VOC sensor) 620 that is electrically connected to a biomarker analyzer (e.g., a VOC analyzer) 630 via, for example, flexible connectors 640 capable of carrying electrical/optical signals. In alternative embodiments, signals may be communicated wirelessly. The flexible connectors 640 may be disposed inside and/or along the length of the catheter 202. The biomarker sensor 620 may be attached to the catheter 202. In one embodiment, the biomarker sensor 620 may be attached near the distal end or tip portion 218 of the catheter 202. Alternatively, the biomarker sensor 620 may be disposed at a distal end of the medical tool 628 discussed above with respect to FIG. 4B. The biomarker analyzer 630 may be included in the teleoperated medical system 100 discussed above with respect to FIG. 1 and may be disposed near or within the master assembly 106 located at the surgeon's console or may be a component of the control system 112. In various embodiments, the biomarker sensor may be located at other locations in or along the instrument system.

The biomarker sensor 620 may be configured to detect and identify biomarkers, such as VOCs, produced by the mass/tumor 510, that exist in the passageways of the patient P's lungs. In one embodiment, the biomarker sensor 620 may be configured to perform gas chromatography and mass spectroscopy (GC-MS) to detect and identify biomarkers (e.g., VOCs) produced by the mass/tumor 510. In other embodiments, the biomarker sensor 620 may be configured to function as, for example, GC-MS with combination of Solid Phase Micro-extraction (SPME), an ion mobility spectrometer, a crystal sensor, a quartz microbalance, a colorimetric analyzer, or a gold particle nanosensor (e.g., multi-walled carbon nanotubes covered with gold, silver, or other noble metal nanoparticles) to detect and identify biomarkers, such as VOCs produced by the mass/tumor 510. Such nanosensors can be constructed to possess a nanostructure, a large surface area, and the noble metal nanoparticles to enhance sensitivity and increase electron-transfer resistance to enhance the performance of the electrochemical sensor. The biomarker sensor 620 may generate electrical/optical signals based on the detection of the VOCs, and communicate the electrical/optical signals over connectors 640 to the biomarker analyzer 630 to indicate presence and a sensed quantity of the biomarkers, such as VOCs. For example, when the biomarker sensor 620 is configured to function as a gold particle nanosensor, resistances of electrodes included in the nanosensor change when exposed to biomarkers, such as VOCs, and the biomarker sensor 620 produces electrical/optical signals based on the change in resistances of the electrodes to indicate the presence of biomarkers, such as VOCs. As the amount of the detected biomarkers, such as VOCs varies, proportional change in resistance and magnitude of electrical/optical signals is analyzed by the biomarker analyzer 630 to indicate the amount of detected biomarkers, such as VOCs. This allows the clinician to discern the change in density of biomarkers, such as VOCs while traversing different passageways of the patient P's lungs 201.

In other words, when a reading indicating increase (e.g., with respect to a previous reading) in the density of the detected biomarkers, such as VOCs is observed, the clinician understands that the biomarker sensor 620, and thereby the distal end 218 of the catheter 202, is traversing closer to the mass/tumor 510. Conversely, when a reading indicating decrease (e.g., with respect to a previous reading) in the density of the detected VOCs is observed, the clinician understands that the biomarker sensor 620, and thereby the distal end 218 of the catheter 202, is traversing away from the mass/tumor 510.

In various embodiments, the biomarker sensor 620 may generate and provide the electrical/optical signals periodically (e.g., every 1 second, 3 seconds, 5 seconds, etc.). Alternatively, the biomarker sensor 620 may generate and provide the electrical/optical signals upon activation by the clinician. For example, the clinician may activate the biomarker sensor 620 every time the position of the distal end 218 of the catheter 202 is changed while traversing the passageway. Alternatively, the biomarker sensor 620 may be positioned at a first location for a predetermined period of time to gather multiple measurements at the first location. After the predetermined period of time has elapsed, the biomarker sensor 620 may be moved to a second location for a predetermined period of time to gather multiple measurements at the second location. Collecting multiple measurements at each location may allow for more accurate filtering of noisy measurements.

In various embodiments, the biomarker sensor 620 can be implemented as an electrochemical (amperometric) sensor that includes a membrane, internal electrolyte solution, a working electrode, a reference electrode, and a counter electrode. A voltage controller is electrically connected to the working electrode and the reference electrode to adequately polarize the working electrode with respect to the reference electrode. A current measurement unit is electrically connected to the working electrode, the voltage controller, and the counter electrode to detect an electrical signal in response to an electrochemical reaction at the working electrode in presence of the biomarkers, such asbVOCs. In operation, analyte particles (e.g., from the biomarkers, such as VOCs detected) can diffuse through the membrane in the electrochemical sensor and the internal electrolyte (e.g., aqueous solution of strong acids, bases, or aprotic solvents) and interact with the working electrode polarized with respect to the reference electrode. The interaction of the analyte particles with the working electrode causes the electrochemical reaction at the working electrode while the counter electrode experiences a reaction that provides electron balance to the electrochemical reaction. This, for example, results in a redox reaction that generates an electrical current that is detected by the current generator.

In various embodiments, biomarker sensor 620 can be implemented as an array of sensors to perform multiple biomarker detection and analysis in parallel. Such sensor arrays can be implemented as a lab-on-a-chip design. Different sensors in the array can be implemented to detect different types of biomarkers (e.g., different VOCs) or different biomarker signatures, for example.

In various embodiments, a target tissue may be located close to the skin surface of the patient and systems and methods described may be used ex-vivo by moving the catheter and sensor in close proximity to the patient's skin or along the patient's skin to detect the tumor through the skin.

Figure 5:
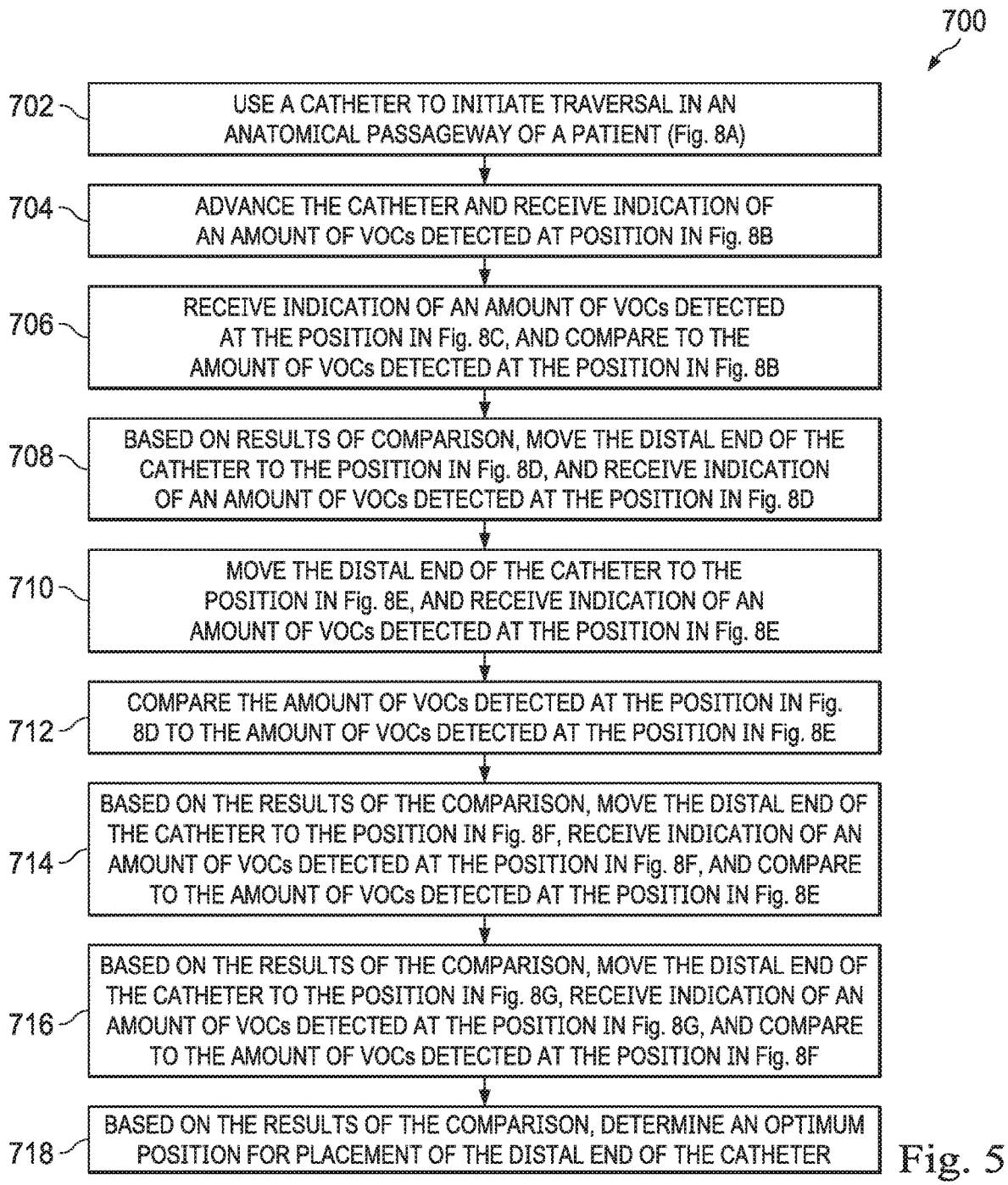
FIG. 5 is a flowchart illustrating a general method 700 used to provide guidance in an image-guided surgical procedure according to an embodiment of the present disclosure.

FIG. 5 is a flowchart illustrating a general method 700 used to provide guidance to a clinician in an image-guided surgical procedure on the patient P in the surgical environment 100, according to an embodiment of the present disclosure. The method 700 is illustrated as a set of blocks, steps, operations, or processes. Not all of the illustrated, enumerated operations may be performed in all embodiments of the method 700. Additionally, some additional operations that are not expressly illustrated in FIG. 5 may be included before, after, in between, or as part of the enumerated processes. For example, method 450 discussed above with respect to FIG. 2 may be performed as part of method 700 to make available the pre-operative or intra-operative image data of, for example, the patient's lungs (FIG. 3). In one embodiment, the image data of the patient's lungs 201 may include representation of the mass/tumor 510 discussed above with respect to FIG. 3. Further, the catheter system 600 may be registered with the available image data of the patient's lungs 201 such that movements of the catheter 202 including the sensor system 510 within the passageways of the patient's lungs 201 are displayed to guide the clinician during the surgical process. Some embodiments of the method 700 include instructions corresponding to the processes of the method 700 as stored in a memory. These instructions may be executed by a processor like a processor of the control system 112.

The movement of the distal end 218 of the catheter 202 is controlled via teleoperational, manual, or automated control (e.g., via master assembly 106) to survey a portion of the anatomical passageways. For example, teleoperational control signals may cause the distal end 218 of the catheter to be directed, advanced, or retracted within the anatomical passageways. As the catheter is moved within the plurality of passageways, a current location of the catheter 202 and/or the distal end 218 in the surgical environment is determined and displayed. The clinician observes movement of the catheter 202 and/or the distal end 218 in the surgical environment on the display (e.g., FIG. 3). FIGS. 6A-6G illustrate the various position of the distal end 218 of the catheter 202 in the passageways of the patient P's lungs.

Figure 6A:
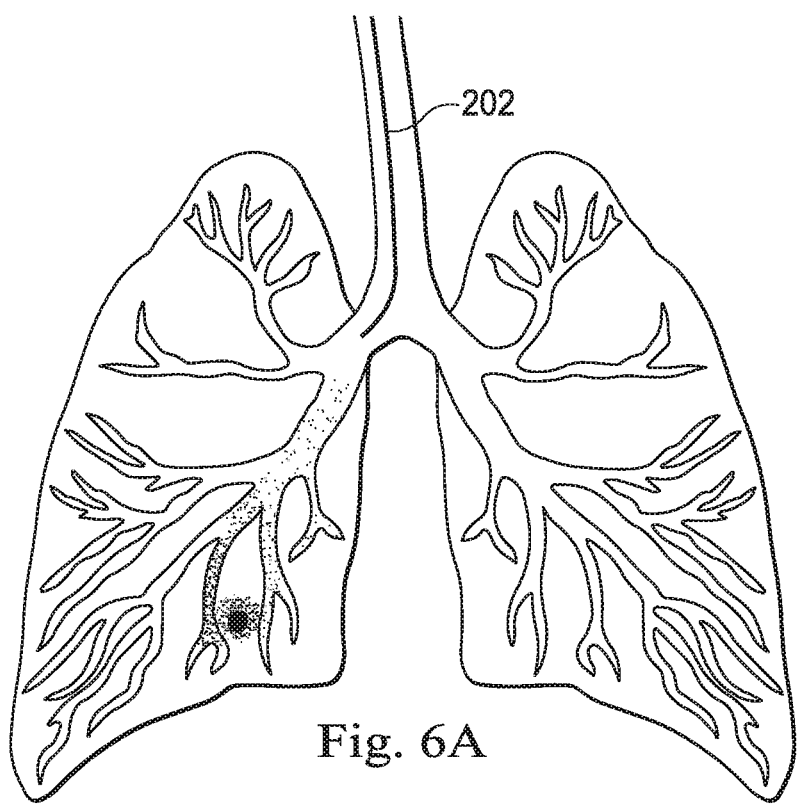
FIGS. 6A-6G illustrate various positions of the distal end of the catheter in anatomical passageways of a patient according to an embodiment of the present disclosure.

At a process 702, the distal end 218 of the catheter 202 is inserted within the patient P's body through, for example, the mouth of the patient P. The distal end 218 of the catheter 202 then traverses the patient P's anatomical passageways (e.g., passageways of the patient's lungs 201). FIG. 6A illustrates an initial position of the distal end 218 of the catheter 202 at an initial location in the patient P's anatomical passageways. Since this initial location of the distal end 218 of the catheter 202 is fairly distant with respect to the mass/tumor 510, the VOC sensor 620 may not detect the presence of VOCs produced by the mass/tumor 510.

Figure 6B:
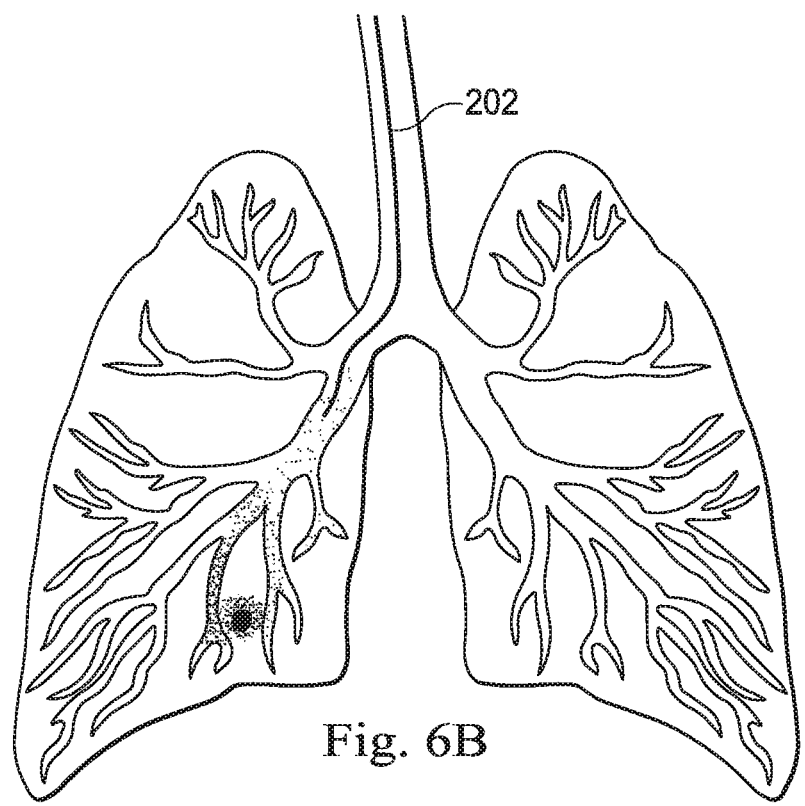

At a process 704, the distal end 218 of the catheter 202 is advanced to the position and location illustrated in FIG. 6B, and the teleoperated medical system 100 receives electrical/optical signals from the VOC sensor 620. In other words, at the location of the distal end 218 of the catheter 202 illustrated in FIG. 6B, the VOC sensor 620 senses and detects the presence of VOCs that exist in the passageways in the vicinity/headspace of the mass/tumor 510. Upon detection of the presence of the VOCs, the VOC sensor 620 generates and communicates electrical/optical signals to the VOC analyzer 630. As discussed previously, the electrical/optical signals generated by the VOC sensor 620 indicate an amount or quantity of VOCs detected at the present location of the VOC sensor 620. At the location of the VOC sensor 620 illustrated in FIG. 6B, the density of the VOCs produced by the mass/tumor 510 is relatively low. However, upon comparison, the processor determines that the density of VOCs at the location illustrated in FIG. 6B is greater with respect to the density of VOCs observed at the location illustrated in FIG. 6A. This increase in the density of detected VOCs indicates to the clinician that the VOC sensor 620 is traversing closer to the mass/tumor 510.

Figure 6C:
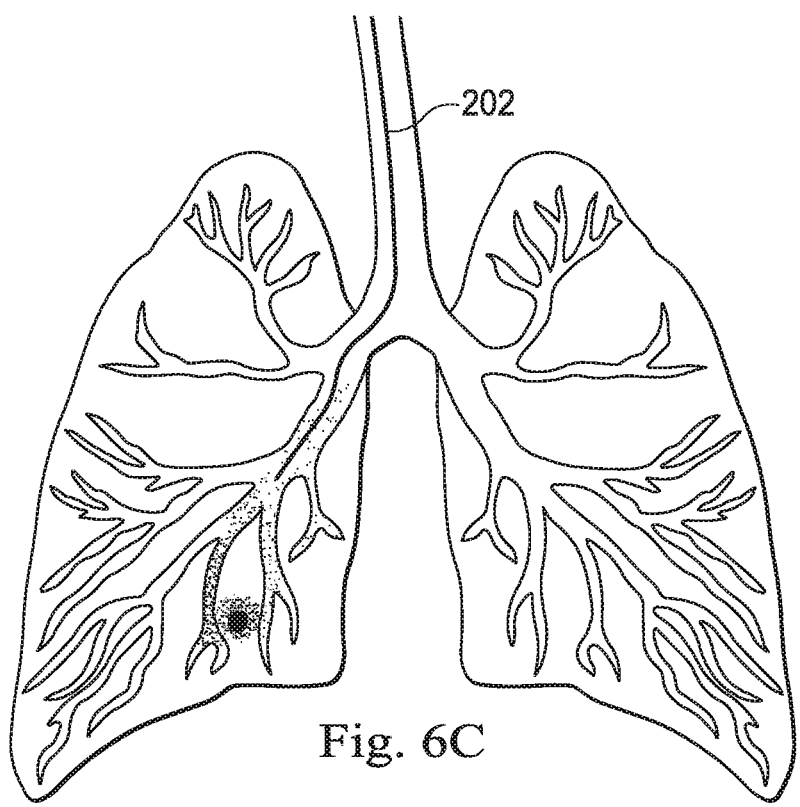

At a process 706, the distal end 218 of the catheter 202 is advanced to the position and location illustrated in FIG. 6C. At this position, the VOC sensor 620 again generates and communicates electrical/optical signals to the VOC analyzer 630 based on the detection of VOCs. At the position of the VOC sensor 620 illustrated in FIG. 6C, upon comparison, the processor determines that the density of the VOCs is greater with respect to the density of VOCs observed at the position illustrated in FIG. 6B. This increase in the density of detected VOCs indicates to the clinician that the VOC sensor 620 is traversing closer to the mass/tumor 510.

Figure 6D:
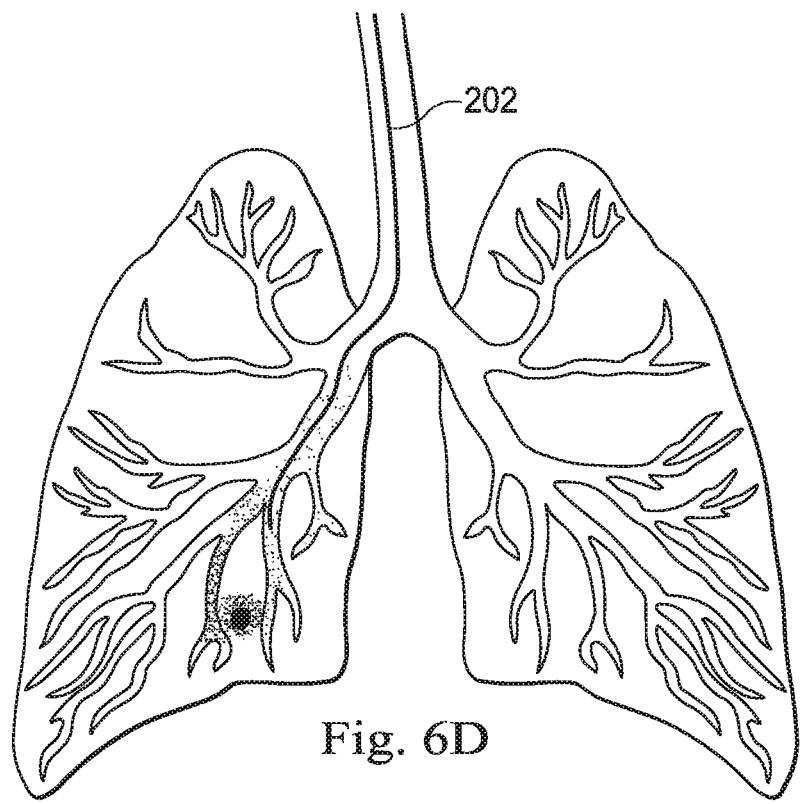
Figure 6E:
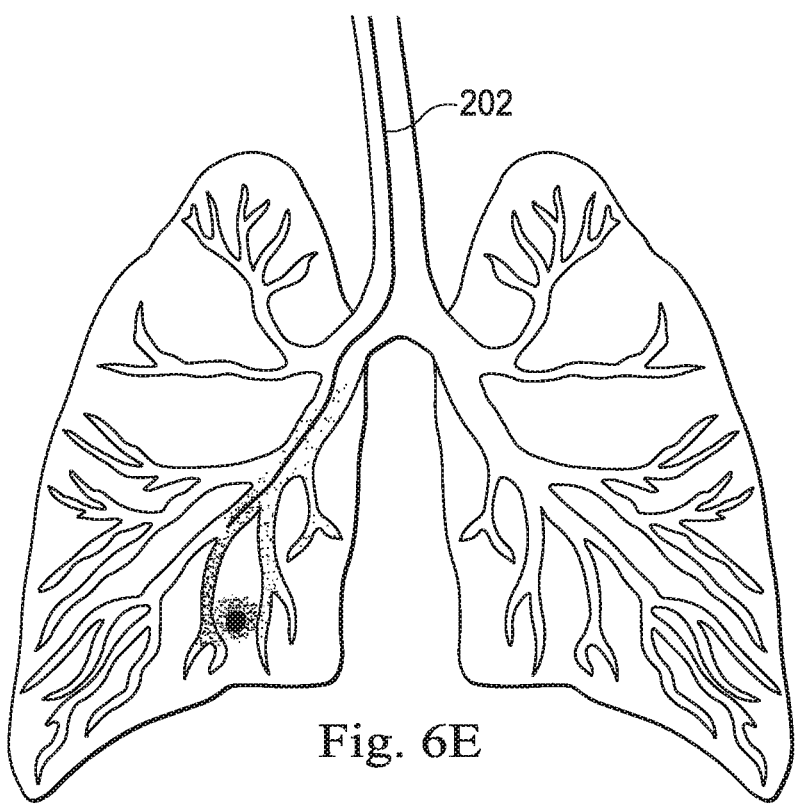

In advancing the distal end 218 of the catheter 202 past the location illustrated in FIG. 6C and towards the mass/tumor 510, the clinician may either advance the catheter 202 along a first passageway towards the location illustrated in FIG. 6D or along a second passageway towards the location illustrated in FIG. 6E. As discussed below, to determine an optimum position and location to biopsy the mass/tumor 510, the clinician may sequentially advance the distal end 218 of the catheter 202 along the first and second passageways. That is, the clinician may choose to advance the distal end 218 of the catheter 202 along the first passageway, and determine a quantity of detected VOCs in the first passageway. Then, the clinician may choose to advance the distal end 218 of the catheter 202 along the second passageway, and determine a quantity of detected VOCs in the second passageway. Based on a comparison of the quantity of the detected VOCs in the first and second passageways, the clinician or processor may determine further positions and locations for advancement of the catheter 202.

At a process 708, the distal end 218 of the catheter 202 is advanced to the location illustrated in FIG. 6D along a first passageway. At this position, the VOC sensor 620 again generates and communicates electrical/optical signals to the VOC analyzer 630 based on the detection of VOCs. At the location of the VOC sensor 620 illustrated in FIG. 6D, upon comparison, the processor determines that the density of the VOCs is greater with respect to the density of VOCs observed at the location illustrated in FIG. 6C. This increase in the density of detected VOCs indicates to the clinician that the VOC sensor 620 is traversing closer to the mass/tumor 510. However, before advancing the distal end 218 of the catheter 202 further along the first passageway, the clinician may advance the catheter 202 along a second passageway to determine the quantity of the detected VOCs in the second passageway.

At a process 710, the distal end 218 of the catheter 202 is advanced to the location illustrated in FIG. 6E along the second passageway. At this location, the VOC sensor 620 again generates and communicates electrical/optical signals to the VOC analyzer 630 based on the detection of VOCs. At the position of the VOC sensor 620 illustrated in FIG. 6E, upon comparison, the processor determines that the density of the VOCs is greater with respect to the density of VOCs observed at the location illustrated in FIG. 6C. This increase in the density of detected VOCs indicates to the clinician that the VOC sensor 620 is traversing closer to the mass/tumor 510. However, to determine the optimum route, the clinician may compare the quantities of the detected VOCs in the first and second passageways before advancing the distal end 218 of the catheter 202 further along the second passageway.

At a process 712, a processor included in the teleoperated medical system 100 compares the quantities of the detected VOCs in the first and second passageways. When the quantity of the detected VOCs in the first passageway is greater than the quantity of the detected VOCs in the second passageway, the system may assist the clinician in determining that the catheter 202 should be advanced along the first passageway. Alternatively, when the quantity of the detected VOCs in the second passageway is greater than the quantity of the detected VOCs in the first passageway, the system may assist the clinician in determining that the catheter 202 should be advanced along the second passageway. In other words, the results of the comparison of the quantities of the detected VOCs in the first and second passageways assist the clinician in determining advancement of the catheter 202 along the passageway that will lead the distal end 218 closest to the mass/tumor 510. For subsequent steps, it is assumed that the results of the comparison indicated that the quantity of the detected VOCs in the second passageway is greater than the quantity of the detected VOCs in the first passageway.

Figure 6F:
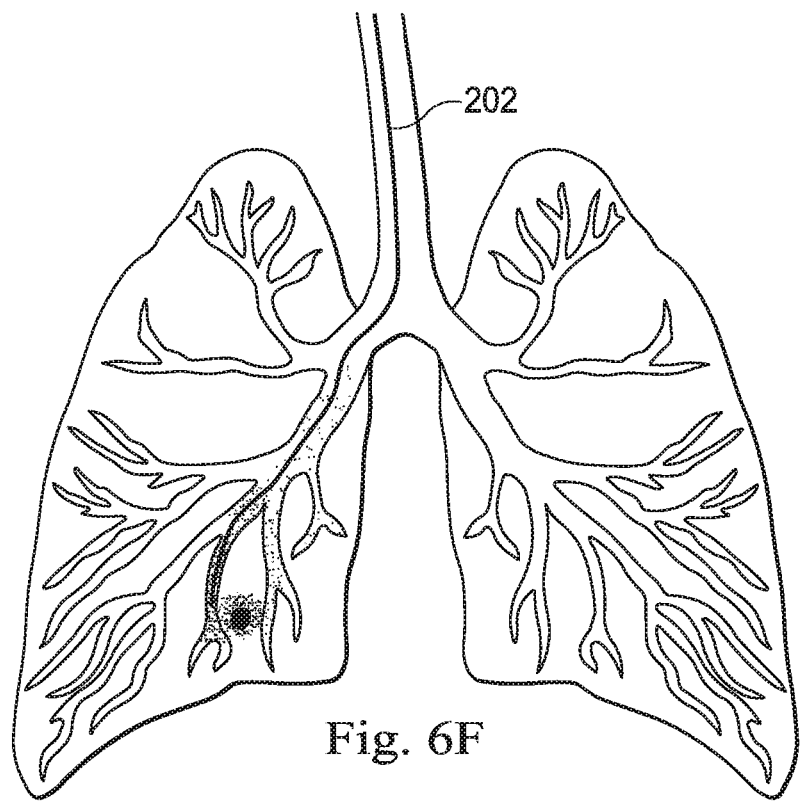

At a process 714, based on the above results of the comparison, the processor or the clinician determines, based on displayed results of the comparison that the distal end 218 of the catheter 202 should be advanced along the second passageway. The advanced location of the distal end 218 of the catheter 202 along the second passageway is illustrated in FIG. 6F. At this location, the VOC sensor 620 again generates and communicates electrical/optical signals to the VOC analyzer 630 based on the detection of VOCs. At the location of the VOC sensor 620 illustrated in FIG. 6F, upon comparison, the processor determines that the density of the VOCs is greater with respect to the density of VOCs observed at the location illustrated in FIG. 6E. This increase in the density of detected VOCs indicates to the clinician that the VOC sensor 620 is traversing closer to the mass/tumor 510. In various alternative examples, based upon the results of the comparisons, the control system 112 may provide guidance or instructions to the clinician to help advance and/or steer the catheter closer to the mass. In various alternative examples, based upon the results of the comparisons, the control system 112 may advance and/or steer the catheter closer to the mass.

Figure 6G:
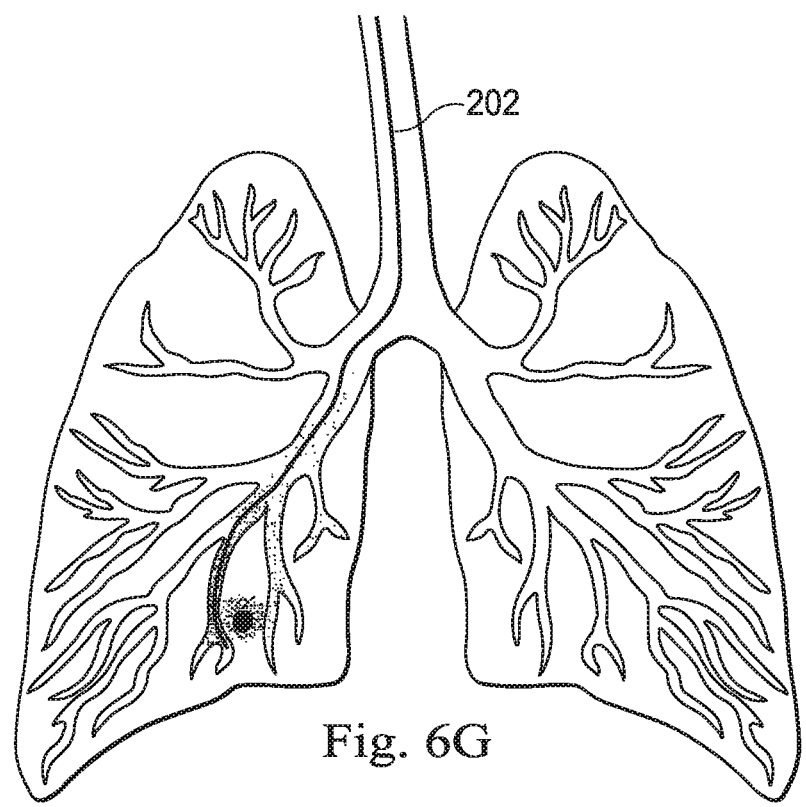

At a process 716, the distal end 218 of the catheter 202 is advanced to the location illustrated in FIG. 6G along the second passageway. At this location, the VOC sensor 620 again generates and communicates electrical/optical signals to the VOC analyzer 630 based on the detection of VOCs. At the location of the VOC sensor 620 illustrated in FIG. 6G, upon comparison, the processor determines that the density of the VOCs is smaller with respect to the density of VOCs observed at the location illustrated in FIG. 6F. This decrease in the density of detected VOCs indicates to the clinician that the VOC sensor 620 is traversing further away from the mass/tumor 510.

Based on the above observations, at a process 718, it is determined that a location in close proximity to the location of the distal end 218 of the catheter 202 illustrated in FIG. 6F represents the optimum location for placement of the distal end 218 of the catheter 202. Further iterations of the above steps of method 700 may be performed to fine-tune the location of the optimum location for placement of the distal end 218 of the catheter 202 for the biopsy. Once the optimum location is determined, the clinician may effect movement of the distal end 218 of the catheter 202 to be placed in the optimum position and location in preparation for the biopsy. The biopsy may then be conducted with the distal end 218 of the catheter 202 being placed in the optimum position and location for the biopsy.

In this way, the sensing/determination of the quantity of the detected VOCs in a plurality of positions and/or locations within the passageways of the patient P's lungs 201 assists in compensating for any difference observed in the physiology of the patient P during the surgical procedure, as discussed above, and in determining the optimum position for placement of the distal end 218 of the catheter 202 for the biopsy procedure.

FIG. 7 is a flowchart illustrating a general method 900 used to provide guidance to a clinician during a surgical procedure on the patient P in the surgical environment 100, according to an embodiment of the present disclosure. Similar to the method 700 discussed above, the catheter system 600 may be coupled with the sensor system 610 capable of sensing and analyzing characteristic VOCs produced by the mass/tumor 510, and may be used in conjunction with method 900. As discussed previously, the sensor system 610 may sense and report a quantity of VOCs in the passageways of the patient's lungs 201 in the vicinity of the mass/tumor 510. Based on the assumption that the density of the VOCs in the passageways is higher closer to the mass/tumor 510, a clinician performing the surgical procedure may navigate different passageways of the patient's lungs, and then determine an optimum position and location in a selected passageway of the patient's lungs 201 for placement and positioning of the catheter 202 closest to the mass/tumor 510 for the biopsy. In other words, based on a gradient of the quantity of VOCs, the sensor system may assist navigation of the different passageways. This may advantageously allow for selection of the optimum location, where the density of the VOCs is sensed to be the highest, for placement of the distal end 218 for the biopsy. In one example, determination of the optimum location may require that the catheter 202 traverse through several generations of passageways to discover passageways in which the density of the VOCs increases progressively. The catheter 202 may traverse a first passageway to determine a density of the VOCs in the first passageway, then may traverse a second next generation passageway to determine whether the density of the VOCs is higher in the second generation passageway with respect to the density of the VOCs in the first passageway. In one example, multiple second generation passageways may lead from the first passageway where the catheter 202 can traverse through each of the multiple second generation passageways to determine the optimum location by determining the highest density of VOCs.

In various embodiments, the traversal of the passageways and the determination of the VOC densities may be used to update the location of the mass/tumor 510 in the registered preoperative model. With the catheter 202 registered to the preoperative model, the determined location in the patient anatomy of the highest density of VOCs may be used to update the preoperative model or to enhance the navigational guidance provided to the clinician via a graphical user interface. The target location of the catheter and the exit point from the airway to the target location may also be updated from the pre-planned target location.

Sometimes, the pre-operative or intra-operative image data in the form of the model 500 of the patient's lungs 201 may not be available to guide the clinician during the surgical procedure. In such cases, vision probes like the ones described in U.S. application Ser. No. 13/274,229 (filed Oct. 14, 2011) (disclosing "Vision Probe Catheter Systems"), which is incorporated herein in its entirety, may be used in conjunction with method 900. Alternatively, the medical tool discussed above may be used in conjunction with the method 900. The medical tool may be an image capture probe that includes a distal portion with a stereoscopic or monoscopic camera at or near the distal end 218 of the flexible catheter body 216. In either case, the vision probe or the medical tool functions as a "visual device" and enables capturing of images (including video images) that are processed by the visualization system 231 for display. In one embodiment, the movement and progress of the catheter 202 is displayed to the clinician from the point of view of the distal end 218 of the catheter 202.

The movement of the distal end 218 of the catheter 202 is controlled via teleoperational, manual, or automated control (e.g., via master assembly 106) to survey a portion of the anatomical passageways. For example, teleoperational control signals may cause the distal end 218 of the catheter to be directed, advanced, or retracted within the anatomical passageways. The visual device when fully deployed in catheter 202 may be placed in a desired orientation at or even extending beyond the distal end 218 of the catheter 202 to provide a forward view from the point of view of the distal end 218 of the catheter 202. The visual device may be remotely steered, and may provide video images of the respiratory tract that may assist the clinician in navigating the distal end 218 towards a target location (e.g., mass/tumor 510). The path followed to the target location may be entirely within natural lumens such as the airways of the respiratory track. As the catheter is moved within the plurality of passageways, a current image from the point of view of the distal end 218 of the catheter 202 in the surgical environment is displayed. The clinician observes movement of the catheter 202 and/or the distal end 218 in the surgical environment on the display. The clinician may effect movement of the catheter 202 along any of the passageways under the guidance of the video images provided by the visual device and the detected VOCs sensed by the sensor system 610.

The method 900 is illustrated as a set of blocks, steps, operations, or processes. Not all of the illustrated, enumerated operations may be performed in all embodiments of the method 900. Additionally, some additional operations that are not expressly illustrated in FIG. 7 may be included before, after, in between, or as part of the enumerated processes. For example, additional steps may be performed to register the catheter system 600 with general image data of human lungs such that movements of the catheter 202 including the sensor system 610 within the passageways of the patient's lungs 201 are displayed. Some embodiments of the method 900 include instructions corresponding to the processes of the method 900 as stored in a memory. These instructions may be executed by a processor like a processor of the control system 112.

At a process 902, a vision probe or the medical tool equipped with a stereoscopic or microscopic camera (i.e., "visual device") is deployed in the catheter 202, and the catheter 202 is inserted within the patient P's body through, for example, the mouth of the patient P, and positioned at an initial location. The distal end 218 of the catheter 202 traverses the patient P's anatomical passageways (e.g., passageways of the patient's lungs 201). As discussed previously, the VOC sensor 620 may provide electrical/optical signals to indicate the presence of VOCs that exist in the passageways in the vicinity/headspace of the mass/tumor 510. At the initial location, the distal end 218 of the catheter 202 may be at a distance from the mass/tumor 510, where the VOC sensor 620 may not detect the presence of VOCs produced by the mass/tumor 510.

At a process 904, the clinician advances the distal end 218 of the catheter 202 past the initial location under the guidance of the video images provided by the visual device to a location in a first passageway.

At a process 906, at this location in the first passageway, the VOC sensor 620 may sense or detect presence of VOCs and provide electrical/optical signals indicating the measured quantity of VOCs. The corresponding measurement at the location in the first passageway may be stored in the memory.

This positive change or increase in the density of detected VOCs indicates to the clinician that the VOC sensor 620, and therefore the distal end 218 of the catheter 202, is traversing closer to the mass/tumor 510. Based on this information, the clinician may decide to further advance the distal end 218 of the catheter 202 along the first passageway. In advancing the distal end 218 of the catheter 202 past the first location and towards the mass/tumor 510, the clinician may either advance the catheter 202 along a second passageway or along a third passageway. In various embodiments, the second and third passageways may be next generation passageways with respect to the first passageway.

At a process 908, the distal end 218 of the catheter 202 is advanced to a location in the second passageway under the guidance of the video images provided by the visual device.

At a process 910, at this location in the second passageway, the VOC sensor 620 generates and communicates electrical/optical signals to the VOC analyzer 630 based on the detection of VOCs. The corresponding measurement of quantities of VOCs detected at the location in the second passageway may be stored in the memory.

At a process 912, the distal end 218 of the catheter 202 is placed in a location in the third passageway under the guidance of the video images provided by the visual device.

At a process 914, at this location in the third passageway, the VOC sensor 620 generates and communicates electrical/optical signals to the VOC analyzer 630 based on the detection of VOCs. The corresponding measurement of quantities of VOCs detected at the location in the third passageway may be stored in the memory.

At a process 916, the processor may retrieve from the memory and compare the measurement at the location in the first passageway to the measurement and the location in the second passageway. The method may progress based on the results of the comparison. For example, the method may progress to a process 918 when the processor determines that the measurement at the location in the first passageway is greater than the measurement at the location in the second passageway. Similarly, the method may progress to a process 920 when the processor determines that the measurement at the location in the first passageway is smaller than the measurement at the location in the second passageway.

At the process 918, the processor may retrieve from the memory and compare the measurement at the location in the first passageway to the measurement and the location in the third passageway. The method may progress based on the results of the comparison. For example, the method may progress to a process 926 when the processor determines that the measurement at the location in the first passageway is greater than the measurement at the location in the third passageway. Similarly, the method may progress to a process 922 when the processor determines that the measurement at the location in the first passageway is smaller than the measurement at the location in the third passageway.

At the process 920, the processor may retrieve from the memory and compare the measurement at the location in the second passageway to the measurement and the location in the third passageway. The method may progress based on the results of the comparison. For example, the method may progress to a process 924 when the processor determines that the measurement at the location in the second passageway is greater than the measurement at the location in the third passageway. Similarly, the method may progress to the process 922 when the processor determines that the measurement at the location in the second passageway is smaller than the measurement at the location in the third passageway.

At the process 922, the processor determines that the location in the third passageway should be the next location of the distal end 218 of the catheter 202. This is based on the results of comparisons at processes 916 and 918 that the measurement of VOCs detected at the location in the third passageway is greater than the measurements of VOCs individually detected at locations in the first and second passageways. The density of detected VOCs at the location in the passageway indicates to the clinician that placing the distal end 218 of the catheter 202 at the location in the third passageway would allow the VOC sensor 620 to traverse closer to the mass/tumor 510. In other words, the results of the comparison of the quantities of the detected VOCs in the different passageways assists in determining advancement of the catheter 202 along the passageway that will lead the distal end 218 closest to the mass/tumor 510

At the process 924, the processor determines that the location in the second passageway should be the next location of the distal end 218 of the catheter 202. This is based on the results of comparisons at processes 916 and 920 that the measurement of VOCs detected at the location in the second passageway is greater than the measurements of VOCs individually detected at locations in the first and third passageways. The density of detected VOCs at the location in the passageways indicates to the clinician that placing the distal end 218 of the catheter 202 at the location in the second passageway would allow the VOC sensor 620 to traverse closer to the mass/tumor 510. In other words, the results of the comparison of the quantities of the detected VOCs in the different passageways assists in determining advancement of the catheter 202 along the passageway that will lead the distal end 218 closest to the mass/tumor 510.

At the process 926, the processor determines that a location other than the locations in the second and third passageways should be the next location of the distal end 218 of the catheter 202. This is based on the results of comparisons at processes 916 and 918 that the measurement of VOCs detected at the location in the first passageway is greater than the measurements of VOCs individually detected at locations in the second and third passageways.

In various embodiments, based upon the results of the comparisons, the control system 112 may provide guidance or instructions to the clinician to help advance and/or steer the catheter closer to the mass/tumor 510. In other embodiments, based upon the results of the comparisons, the control system 112 may advance and/or steer the catheter closer to the mass/tumor 510.

Further iterations of the above processes of method 900 may be performed to fine-tune the location of the optimum position for placement of the distal end 218 of the catheter 202 for the biopsy. The biopsy may then be conducted with the distal end 218 of the catheter 202 being placed in the optimum position for the biopsy.

The distal end 218 of the catheter 202 may be sequentially advanced along the second and third passageways to determine an optimum position and location to biopsy the mass/tumor 510. That is, the clinician may choose to advance the distal end 218 of the catheter 202 along the second passageway, and determine a quantity of detected VOCs in the second passageway. Then, the clinician may choose to advance the distal end 218 of the catheter 202 along the third passageway, and determine a quantity of detected VOCs in the third passageway. Based on a comparison of the quantity of the detected VOCs in the second and third passageways, the clinician may determine further locations for advancement of the catheter 202.

In this way, in the absence of the pre-operative or intra-operative image data, the distal end 218 of the catheter 202 may be placed in various positions within the passageways of the patient P's lungs under the guidance of the video images provided by the visual device. Further, at these various positions, the quantity of the VOCs may be sensed/determined with the help of the sensor system 610. This facilitates determination of the optimum position for placement of the distal end 218 of the catheter 202 for the biopsy procedure.

Similar to the detection and analysis of VOCs discussed above, the present disclosure contemplates detection and analysis of other biomarkers produced in the vicinity of the mass/tumor by changes in, for example, pressure, oxygen, and a pH level. For instance, the sensor system 610 may include a pressure sensor to sense biomarkers produced as a result of change in a level of pressure in the vicinity of the mass/tumor. Comparative measurements of these biomarkers may be used determine locations for treatment or other interventional procedures and described above for methods 700, 900. Physiologically, due to the presence of the mass/tumor, there may be uncharacteristic change (increase or decrease) in the pressure in the anatomical passageways in the vicinity of the mass/tumor. This uncharacteristic change in pressure may change the density of the biomarkers. For example, the density of these biomarkers may be greater in areas of high pressure closer to the mass/tumor, and be lower in areas of low pressure relatively further away from the mass/tumor. The pressure sensor may enable precise detection of a location of a mass/tumor in a patient's body by sensing and analyzing the density of these biomarkers similar to that of VOCs discussed above.

In another embodiment, the sensor system 610 may include an oxygen sensor to sense biomarkers produced as a result of change in a level of oxygen in the vicinity of the mass/tumor. Comparative measurements of these biomarkers may be used determine locations for treatment or other interventional procedures and described above for methods 700, 900. Physiologically, due to the presence of the mass/tumor, there may be uncharacteristic change (increase or decrease) in the level of oxygen in the anatomical passageways in the vicinity of the mass/tumor. This uncharacteristic change in oxygen level may change the density of the biomarkers. For example, the density of the oxygen biomarkers may be greater in areas having a low level of oxygen (causing apoxia) closer to the mass/tumor, and be lower in areas having a higher level of oxygen relatively further away from the mass/tumor. The oxygen sensor may enable precise detection of a location of a mass/tumor in a patient's body by sensing and analyzing the density of these biomarkers similar to that of VOCs discussed above.

The sensor system 610 may alternatively include a pH sensor to sense biomarkers produced as a result of change in a pH level in the vicinity of the mass/tumor. Comparative measurements of these biomarkers may be used determine locations for treatment or other interventional procedures and described above for methods 700, 900. Physiologically, due to the presence of the mass/tumor, there may be uncharacteristic change (increase or decrease) in the pH level in the anatomical passageways in the vicinity of the mass/tumor. This uncharacteristic change in the pH level may change the density of the biomarkers. For example, the density of the pH biomarkers may be greater in areas having a low pH level (acidic environment) closer to the mass/tumor, and be lower in areas having a high pH level relatively further away from the mass/tumor. The pH sensor may enable precise detection of a location of a mass/tumor in a patient's body by sensing and analyzing the density of these biomarkers similar to that of VOCs discussed above.

The sensor system 610 may also include a fluoro sensor to sense fluoroscopic biomarkers produced by the mass/tumor. Comparative measurements of these biomarkers may be used determine locations for treatment or other interventional procedures and described above for methods 700, 900. Physiologically, the mass/tumor may produce fluoroscopic biomarkers in the anatomical passageways in the vicinity of the mass/tumor. The density of the fluoroscopic biomarkers may be greater in areas closer to the mass/tumor, and be lower in areas further away from the mass/tumor. The fluoro sensor may enable precise detection of a location of a mass/tumor in a patient's body by sensing and analyzing the density of these fluoroscopic biomarkers similar to that of VOCs discussed above.

Although the above embodiments describe use of one VOC sensor, in all embodiments, the catheter system 600 may be coupled with the sensor system 610 that includes a plurality of VOC sensors. Features of this plurality of VOC sensors may be similar to the features of VOC sensor 620, discussed above. The plurality of VOC sensors may be attached to the catheter 202. For instance, a first VOC sensor may be attached near the distal end or tip portion 218 of the catheter 202 while a second VOC sensor may be attached to the catheter 202 proximally in a spaced relationship with respect to the first VOC sensor. In this way, multiple biomarker measurements can be obtained at a given location and position of the catheter 202 within the patient's anatomy. The multiple biomarker measurements may be compared with each other to determine the optimum location and position for placement of the distal end 218 of the catheter 202 for the biopsy procedure, as discussed previously. In addition to determining the optimum location and position for placement of the distal end 218 of the catheter 202, the multiple biomarker measurements may be obtained in various anatomical passages of the patient anatomy to create a pre-operative model indicating presence of various levels and quantities of VOCs within the patient anatomy.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. Also, although the systems and methods of this disclosure have been described in connection with detecting the precise location of a mass/tumor for the purposes of conducting a biopsy, the presently disclosed systems and methods may also be used for purposes of delivering treatment. For example, the present systems and methods may be used for delivering pharmaceutical medication or for delivering radiation treatment to precise locations in anatomical passageways within a patient's body. In various embodiments, the delivery of pharmaceutical medication or radiation treatment may be tele-operatively or automatically performed under the control of the tele-operated medical system of FIG. 1.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method for guiding a medical instrument towards a target, comprising:
    positioning the medical instrument at a first location, wherein the medical instrument comprises at least one sensor;
    determining a first biomarker measurement using the at least one sensor;
    determining a second biomarker measurement using the at least one sensor;
    comparing, by a processor, the first biomarker measurement with the second biomarker measurement to determine a proximity to the target to provide a first comparison; and
    providing guidance for moving the medical instrument based on results of the first comparison.

2. The method of claim 1, wherein the guidance for moving of the medical instrument includes directing retraction, advancement, or steering of the medical instrument towards the target.

3. The method of claim 1, wherein providing guidance includes guiding the medical instrument to advance when the second biomarker measurement is greater than the first biomarker measurement, wherein the first biomarker measurement and the second biomarker measurement are measurements of densities of biomarkers.

4. The method of claim 1, wherein providing guidance includes guiding the medical instrument to retract when the first biomarker measurement is greater than the second biomarker measurement, wherein the first biomarker measurement and the second biomarker measurement are measurements of densities of biomarkers.

5. The method of claim 1, wherein providing guidance includes providing video images provided by a visual device disposed at a distal end of the medical instrument.

6. The method of claim 1, wherein the determining the first biomarker measurement includes receiving a first electrical or optical signal from the at least one sensor indicating a first quantity of biomarkers detected at a first location, and the determining the second biomarker measurement includes receiving a second electrical or optical signal from the at least one sensor indicating a second quantity of biomarkers detected at a second location.

7. The method of claim 6, wherein receiving the first and second electrical or optical signals includes receiving the first and second electrical or optical signals periodically.

8. The method of claim 6, wherein the receiving the first and second electrical or optical signals includes receiving the first and second electrical or optical signals upon activation of the at least one sensor.

9. A system, comprising:
a medical instrument configured to be positioned at a first location within a patient anatomy;
at least one sensor coupled to the medical instrument, the at least one sensor being configured to determine a first biomarker measurement and a second biomarker measurement; and
a processor configured to:
compare the first biomarker measurement with the second biomarker measurement to determine a proximity to a target within the patient anatomy; and
based on the comparing the first biomarker measurement with the second biomarker measurement, provide guidance for moving the medical instrument towards the target.

10. The system of claim 9, wherein the at least one sensor includes a first sensor and a second sensor, wherein the first sensor is disposed proximally to the second sensor along a length of the medical instrument, and wherein the first sensor is configured to provide the first biomarker measurement and the second sensor is configured to provide the second biomarker measurement.

11. The system of claim 9, wherein the guidance for moving the medical instrument includes directing advancement, retraction, or steering of the medical instrument towards the target.

12. The system of claim 9, further comprising:
a visual device disposed at a distal end of the medical instrument, wherein the processor is configured to provide video images provided by the visual device.

13. The system of claim 9, wherein
to determine the first biomarker measurement, the at least one sensor is configured to sense a first electrical or optical signal indicating a first quantity of biomarkers detected at a first location, and
to determine the second biomarker measurement, the at least one sensor is configured to sense a second electrical or optical signal indicating a second quantity of biomarkers detected at a second location.

14. The system of claim 9, wherein the first biomarker measurement and the second biomarker measurement are associated with a quantity of volatile organic compounds (VOCs) within the patient anatomy.

15. The system of claim 9, wherein the target is a mass or a tumor within the patient anatomy.

16. The system of claim 9, wherein the at least one sensor includes a gas chromatography and mass spectroscopy sensor.

17. The system of claim 16 wherein the at least one sensor includes a solid phase microextraction sensor, an ion mobility spectrometer, a crystal sensor, a quartz microbalance, a colorimetric analyzer, or a gold particle nanosensor.

18. The system of claim 9, wherein the at least one sensor includes an electrochemical sensor.

19. The system of claim 9, wherein the at least one sensor includes a sensor array.

20. A non-transitory machine-readable medium comprising a plurality of machine-readable instructions which when executed by one or more processors associated with a medical device are adapted to cause the one or more processors to perform a method for guiding a medical instrument towards a target, the method comprising:
positioning the medical instrument at a first location, wherein the medical instrument comprises at least one sensor;
determining a first biomarker measurement using the at least one sensor;
determining a second biomarker measurement using the at least one sensor;
comparing the first biomarker measurement with the second biomarker measurement to determine a proximity to the target to provide a first comparison; and
providing guidance for moving the medical instrument based on results of the first comparison.

* * * * *